(12) United States Patent
Schurr et al.

(10) Patent No.: US 11,076,855 B2
(45) Date of Patent: Aug. 3, 2021

(54) PARTLY RESORBABLE TISSUE CLIP (71) Applicant: Ovesco Endoscopy AG, Tubingen (DE)

(72) Inventors: Marc Schurr, Tubingen (DE); Gunnar Anhock, Reutlingen (DE)

(73) Assignee: Ovesco Endoscopy AG

( * ) Notice: Subject to any disclaimer, the term of this patent is extended or adjusted under 35 U.S.C. 154(b) by 0 days.

(21) Appl. No.: 15/501,810

(22) PCT Filed: Jul. 30, 2015

(86) PCT No.: PCT/EP2015/067496
§ 371 (c)(1),
(2) Date: Feb. 3, 2017

(87) PCT Pub. No.: WO2016/020259
PCT Pub. Date: Feb. 11, 2016

(65) Prior Publication Data
US 2017/0231630 A1    Aug. 17, 2017

(30) Foreign Application Priority Data

Aug. 4, 2014  (DE) .......................... 102014111038.2

(51) Int. Cl.
| | | |
|---|---|---|
| *A61B 17/08* | (2006.01) | |
| *A61L 31/14* | (2006.01) | |
| *A61B 17/064* | (2006.01) | |
| *A61L 31/02* | (2006.01) | |
| *A61L 31/06* | (2006.01) | |
| *A61B 17/00* | (2006.01) | |

(52) U.S. Cl.
CPC .......... *A61B 17/083* (2013.01); *A61B 17/064* (2013.01); *A61B 17/08* (2013.01);
(Continued)

(58) Field of Classification Search
CPC .... A61L 31/148; A61L 31/022; A61L 31/028; A61L 31/06; A61B 17/083;
(Continued)

(56) References Cited

U.S. PATENT DOCUMENTS

| | | |
|---|---|---|
| 5,630,452 A | 5/1997 | Schmid et al. |
| 6,849,078 B2 | 2/2005 | Durgin et al. |

(Continued)

FOREIGN PATENT DOCUMENTS

| | | |
|---|---|---|
| DE | 3879990 T2 | 9/1993 |
| DE | 29923545 U1 | 11/2000 |

(Continued)

OTHER PUBLICATIONS

Office Action issued in parallel Japanese patent application 2017-506774 dated Jul. 11, 2017.
(Continued)

*Primary Examiner* — Kathleen S Holwerda
*Assistant Examiner* — Brooke Labranche
(74) *Attorney, Agent, or Firm* — RatnerPrestia (57) ABSTRACT

A partly resorbable tissue clip for stapling tissue includes at least one gripping tooth that grips the tissue, at least one force deflecting element that is equipped with at least one gripping tooth, and at least one spring element that is connected to the at least one force deflecting element. The at least one gripping tooth or a portion of the at least one force deflecting element or of at least one of the force deflecting elements is made of bioresorbable material.

14 Claims, 7 Drawing Sheets

(52) U.S. Cl.
CPC ........... *A61L 31/022* (2013.01); *A61L 31/028* (2013.01); *A61L 31/06* (2013.01); *A61L 31/148* (2013.01); *A61B 2017/00004* (2013.01); *A61B 2017/00818* (2013.01); *A61B 2017/00893* (2013.01); *A61B 2017/0645* (2013.01); *A61B 2017/081* (2013.01)

(58) Field of Classification Search
CPC .... A61B 2017/00004; A61B 2017/081; A61B 2017/083; A61B 2017/085; A61B 17/064; A61B 2017/00818; A61B 2017/0645
See application file for complete search history.

(56) References Cited

U.S. PATENT DOCUMENTS

| | | | | |
|---|---|---|---|---|
| 2004/0087987 | A1* | 5/2004 | Rosenberg | A61B 17/12 606/157 |
| 2012/0059394 | A1* | 3/2012 | Brenner | A61B 1/00087 606/142 |
| 2013/0289586 | A1* | 10/2013 | Mazzucco | A61B 17/083 606/151 |

FOREIGN PATENT DOCUMENTS

| | | |
|---|---|---|
| DE | 102005041093 A1 | 11/2016 |
| EP | 2449983 A1 | 5/2012 |
| JP | 2003-518975 A | 6/2003 |
| JP | 2006-512157 A | 4/2006 |
| JP | 2012-517858 A | 8/2012 |

OTHER PUBLICATIONS

European Patent Office, International Search Report for PCT/EP2015/067496 dated Oct. 8, 2015.
German Patent and Trademark Office, German Search Report for application No. DE 102014111038.2 dated May 27, 2015.
European Patent Office, Communication Under Rule 71(3) EPC in application No. 15745453.9 dated Apr. 1, 2016.

* cited by examiner

PARTLY RESORBABLE TISSUE CLIP

CROSS-REFERENCE OF RELATED APPLICATION

This application is a U.S. National Stage of application number PCT/EP2015/067496, filed on Jul. 30, 2015, which is based on European Application number 157454539.9 filed Jul. 30, 2015, both of which claim priority to German Application number 102014111038.2 filed on Aug. 4, 2014, of which is incorporated by reference herein its entirety.

The present invention relates to a partly resorbable tissue clip for stapling tissue of a human or animal body which is designed in such a way that as a result of resorption of a resorbable portion of the tissue clip the clamping effect of the tissue clip decreases over time without fragmentation (i.e. without the tissue clip disintegrating into individual metal fragments) until the tissue clip detaches itself automatically from the tissue and can be eliminated from the body without further surgical intervention, for example in the case of surgical, gastroenterological or proctological procedures.

BACKGROUND TO THE INVENTION

In modern endoscopy or surgery, tissue clips are used to clamp off sections of tissue prior to the surgical removal of these sections of tissue in order to arrest bleeding or to staple surgically separated sections of tissue. In gastroenterological or proctological surgery, for example, a lesion in a section of the intestine can be clamped off or bleeding of tissue can be reduced during and after the intervention. Furthermore, a tissue clip can also be used to staple the existing wound margins after removal of a portion of the wall of the digestive tract so as to accelerate wound healing and prevent the contents of the stomach and intestine from escaping into the abdominal cavity. In order to reliably close an incision in the intestine, for example, a tissue clip has to exert a certain force on the two stapled pieces of tissue. This makes high demands of the mechanical material properties of the tissue clip. Due to the excellent mechanical properties of non-resorbable medical materials such as titanium, nickel-titanium alloys and non-oxidizing spring steels, conventional tissue clips are usually made out of this kind of non-bioresorbable but tissue-compatible material.

However, producing a tissue clip out of a non-bioresorbable material involves the disadvantage of having to remove the tissue clip that has been inserted in the body, if necessary by means of surgical intervention, after the stapled tissue has healed. This means that, in addition to the intervention to insert the tissue clip, a second intervention may be necessary to remove the tissue clip. In order to avoid this necessity of a second surgical intervention to remove the tissue clip, the tissue clip can be made wholly or partly out of bioresorbable material.

STATE OF THE ART

A completely bioresorbable tissue clip is known from DE 29923545 U1, for example. This tissue clip is used in particular in the case of hernia operations to fix a plastic mesh inserted in the abdominal cavity to the abdominal wall until the plastic mesh adheres inseparably to the abdominal wall. The tissue clip consists of a body made of resorbable material with a shoulder, guide axes and rotational axes and with one gripping tooth at each end of the shoulder respectively which protrudes vertically from the shoulder. A knee lever is embedded centrally in the shoulder to bend the shoulder. When the knee lever is pressed into a stable extended position, the shoulder is bent as a result and the two gripping teeth close in the clamp slit for tissue formed between the gripping teeth. The clamping force which anchors the gripping teeth in the tissue is applied by the leverage effect of the knee lever.

For many endoscopic or surgical applications, however, it is advantageous when the clamping force which anchors the gripping teeth of the tissue clip in the tissue is applied automatically by means of a spring effect, as described for example in U.S. Pat. No. 6,849,078 B2. This has the advantage, for example, that the tissue clip in this case can be introduced to the tissue for stapling in a position with preloaded spring elements and opened clamp slit, for example on the tip of an endoscope, and the preloaded tissue clip, when applied to the tissue, automatically anchors itself in the tissue due to the spring effect of the preloaded spring elements when the endoscope is withdrawn again and the tissue clip is no longer secured in the opened position with preloaded spring elements by means of an application device. An additional application of pressure to the tissue clip (for example as required to push a knee lever into place) is thus not required in the case of this tissue clip with spring elements as an automatic closing mechanism. This permits the use of a tissue clip with spring elements even in the case of sensitive tissue types or in regions which are difficult to access endoscopically or surgically, where the external application of a clamping pressure onto the tissue clip proves difficult.

Due to the often inadequate mechanical properties of bioresorbable material, however, it is very difficult to design a tissue clip with an automatic closing mechanism preferably in the form of spring elements which are fully resorbable because at least the spring elements have to be made of a different non-bioresorbable, tissue-compatible material with better mechanical properties (e.g. spring steel or a shape memory alloy).

In order to provide the necessary mechanical properties for any spring elements in the tissue clip but still achieve the benefits of a resorbable tissue clip, tissue clips can essentially only be partly made of bioresorbable material. In these partly resorbable tissue clips, a portion of the tissue clip is made of a bioresorbable material and another portion is made of a tissue-compatible, non-resorbable material.

The clamping force of such a partly resorbable tissue clip, by means of which the latter holds together two sections of tissue and is held onto the tissue itself, decreases with increasing resorption of the portion of the tissue clip which is made of bioresorbable material, until the point is reached at which the tissue clip automatically detaches itself from the tissue and the remaining portion made of non-bioresorbable material can be eliminated without further intervention, for example, at usage in the digestive tract.

In the case of partly resorbable tissue clips, however, the fundamental problem applies that after resorption of the bioresorbable portion of the tissue clip, the portion of the tissue clip made of non-resorbable material disintegrates into a number of small fragments (it becomes fragmented), and these fragments can be too small for the body to eliminate in the normal way and can therefore remain in the digestive tract or can cause damage to the intestine due to their sharp-edged nature.

BRIEF DESCRIPTION OF THE INVENTION

Based on the above description of the state of the art, the object of the invention is to create a partly resorbable tissue clip which itself provides the necessary clamping force for a reliable stapling of two portions of an intestinal wall, for example, and can also be used with sensitive tissue, but due to its bioresorbable portions avoids the potential necessity of a second surgical intervention to remove the tissue clip and can also be eliminated from the body unproblematically.

This object is achieved by a tissue clip with the features according to claim 1. Advantageous embodiments of the invention are the subject of the dependent claims.

The core idea of the present invention is therefore to make the tissue clip from a resorbable material in those areas outside its automatic effecting closing mechanism (spring elements). These areas are selected in such a way that the tissue clip continues to remain in one piece after the resorbable material has dissolved and yet the gripping/holding effect on the patient tissue is at least reduced/suspended to such an extent that the tissue clip preferably easily detaches itself independently from the patient tissue.

The core idea according to the invention can be implemented in terms of design in that the areas of the tissue clip which are provided for the immediate clamp/grip operation or contact with the patient tissue and/or the areas that transfer the clamp/grip force (which are preferably arranged in immediate proximity to the contact areas and therefore support/stiffen the contact areas) are at least made of the resorbable material in portions so that after resorption the gripping effect of the tissue clip is suspended or weakened. The tissue clip is preserved at least in its basic structure/frame and does not disintegrate into individual parts/fragments.

Such a partly resorbable tissue clip for stapling tissue comprises a number of gripping teeth which grip the tissue and are attached to a number of force deflecting elements (toothed racks/jaws) situated opposite one another. In this way, a clamp slit for clamping tissue is formed between the gripping teeth. The force deflecting elements are essentially preferably elongated, further preferably curved plates/platelets whose longitudinal axis runs at right angles to the respective longitudinal axis of the gripping tooth formed on it and which serve to absorb the clamping/gripping force applied by the clamping of tissue between the gripping teeth onto the gripping teeth and conduct this force as a thrust into the tissue clip. In order to apply the gripping force necessary for reliable stapling of tissue sections, the force deflecting elements are connected with spring elements (preferably single-section/unitary or also multiple-section/multipart elements formed on the force deflection elements) which mutually preload the force deflecting elements situated opposite each other.

According to a preferred aspect of the invention, gripping teeth of the tissue clip are now made of bioresorbable material.

With increasing resorption of the gripping teeth, the contact surface between the gripping teeth and the tissue clamped between the gripping teeth is reduced, and as a result also the clamping force which keeps the tissue clip on the tissue. When the size of the contact surface or the clamping force falls below a certain level, the remaining portion of the tissue clip (i.e. the portion not made of resorbable material, possibly with partially a still unresorbed portion made of resorbable material attached to it) detaches itself from the tissue and can be eliminated whole by the body in the normal way, for example in the case of application in the digestive tract.

According to a second aspect of the invention, a portion of at least one force deflecting element is made of bioresorbable material for the purpose of selective material weakening of this force deflecting element.

The increasing resorption of the bioresorbable portion of the at least one force deflecting element involves selective material weakening of the force deflecting element. In this way, the clamping/gripping force acting on the gripping teeth can no longer be conducted from the gripping teeth into the rest of the body of the tissue clip and into the spring elements, i.e. the force deflection elements can no longer resist the clamping/gripping force and they become deformed. As a result, the clamping/gripping force introduced to the gripping teeth by the spring elements is reduced. The tissue clip thus easily becomes detached from the patient tissue with increasing resorption of the portion of the at least one force deflecting material made of bioresorbable material and can be eliminated as a whole.

According to another aspect of the invention, the tissue clip is designed in the shape of a mouth section (shark's mouth), whereby the force deflecting elements form an upper and a lower jaw which are elastically connected to each other on their longitudinal sides by means of the spring elements so as to allow automatic closing/gripping. The spring elements can be configured in such a way that they perform both the function of the closing mechanism (preload elements) and at the same time that of pivot hinges. In other words, the upper and lower jaw are solely coupled to one another via the spring elements. As an alternative to this, it is also possible to couple the jaws via pivot hinges (hinge pins and eyelets) and apply the preload force via separate spring elements parallel to the pivot hinges.

In addition to the portion made of bioresorbable material (gripping teeth and/or portion of a force deflecting element), the tissue clip also comprises a portion made of non-bioresorbable, tissue-compatible material. This portion made of non-bioresorbable, tissue-compatible material serves to ensure the necessary mechanical properties, for example a high degree of spring elasticity and bending strength in the tissue clip.

In one embodiment, the portion of the tissue clip made of non-bioresorbable, tissue-compatible material is made as a single piece/integrally, preferably by means of injection moulding (metal injection moulding) or cut out of a spring steel sheet, in particular punched/lasered. The preferably one-piece manufacture of the non-bioresorbable portion of the tissue clip simplifies the production method of the tissue clip and improves the mechanical properties of the tissue clip, such as its bending strength. At this point it should be particularly noted that the clip (i.e. its metal body) can also be realized in a multiple-section/multi-piece design, for example with two jaws hinged together (pin-eyelet design), by means of which other advantages could be achieved such as the improvement of spring characteristics, etc.

Since the tissue clip has to be stable and rigid in itself, the portion made of bioresorbable material has to be permanently fixed to the portion made of non-bioresorbable but tissue-compatible material. In one embodiment, therefore, the portion made of bioresorbable material is connected by means of interlocking/form closure and/or friction-locking/frictional connection with the portion made of non-bioresorbable, tissue-compatible material. It can also be bonded or welded, however. For example, gripping teeth can be studded/riveted or pinned onto the force deflecting elements. The material weakenings in the area of the force deflecting elements could be achieved by the force deflecting elements comprising several of a kind of window openings which are filled by the resorbable material. When the material dissolves, the force deflection elements remain as window frames, so to speak, and can no longer absorb thrust forces/shear forces.

In one embodiment, the non-bioresorbable, tissue-compatible material is nitinol. The bioresorbable material can be a copolymer made of lactic and glycolic acid (PLGA), hydroxyapatite (HPA), beta-tricalcium phosphate or tricalcium phosphate (TCP). Materials such as polylactide (polylactic acids), PLGA (a kind of derivative of these), etc. would also be conceivable.

By selecting a specific bioresorbable material or by adjustment of the composition of the bioresorbable material, the resorption rate of the bioresorbable material can be adapted, thereby adapting the time at which the tissue clip detaches itself from the tissue.

Furthermore, the bioresorbable material can contain medicinal active agents or medications which are released locally over time through resorption of the bioresorbable material or diffusion from this bioresorbable material. In this way, the tissue clip can also be used as part of the in-situ administration of medication.

The shape of the portion of the tissue clip made of bioresorbable material can be adapted to the requirements of the application in question. For example, the gripping teeth made of bioresorbable material can be varied in their length, width or curve. In addition to the gripping teeth, the portion of the tissue clip made of bioresorbable material can also comprise a bioresorbable plate on/against which the gripping teeth are attached/formed and which runs essentially parallel to the at least one force deflecting element. In order to fix the toothed plate made of bioresorbable material to the non-bioresorbable portion of the force deflecting elements, the plate can furthermore comprise a recess in which the force deflecting element of the non-bioresorbable portion is embedded. In addition, the plate can comprise at least one protrusion which engages in the cut-out/recess of the non-bioresorbable portion.

In the case of selective material weakening of the at least one force deflecting element by the fact that a portion of the force deflecting element is made of bioresorbable material, the shape of the bioresorbable portion can also be tailored to the respective needs of a specific application. Here, the bioresorbable portion of a tissue clip can also consist of any desired combination of differently shaped elements.

In one embodiment, the portion of the at least one force deflecting element made of bioresorbable material is essentially configured as a flat, rectangular plate whose longitudinal axis runs parallel to the clamp slit for tissue formed by the gripping teeth. The portion made of non-bioresorbable material of the at least one force deflecting element comprises an appropriate cut-out (window opening) in which the bioresorbable portion of the at least one force deflecting element is preferably embedded/inserted by means of interlocking or friction-locking.

In another embodiment, the portion of the at least one force deflecting element made of bioresorbable material is configured as a number of serially arranged flat plates whose longitudinal axis runs parallel to the clamp slit for tissue formed by the gripping teeth. The portion of the at least one force deflecting element made of non-bioresorbable material comprises a number of relevant cut-outs, whereby at least one flat plate of the bioresorbable portion of the at least one force deflecting element is preferably embedded by means of interlocking or friction-locking in a cut-out of the non-bioresorbable portion.

Alternatively or in addition to the flat plates of the bioresorbable portion of the relevant cut-outs, the portion made of non-bioresorbable material comprises a cut-out in the shape of an elongated hole or several cut-outs in the form of elongated holes arranged in series, wherein the longitudinal axis of each elongated hole runs essentially parallel to the clamp slit for tissue formed by the gripping teeth. An elongated hole here refers to a cut-out whose narrow sides are each closed by semicircles whose diameter is equal to the width of the elongated hole, wherein the longitudinal sides of the elongated hole run parallel to each other. A circular or elliptical shape would also be conceivable. The bioresorbable portion here is configured as one or more flat plates, wherein a plate refers to a resorbable portion in which the narrow sides of the plate are each closed by a semicircle. Each plate of the bioresorbable portion is therefore equal to a cut-out in the form of an elongated hole of the non-bioresorbable portion.

In a further embodiment, the portion of the at least one force deflecting element made of bioresorbable material is configured as a number of plates, wherein each plate is embedded in the relevant cut-out in the non-bioresorbable portion. Here the number of plates is equal to the number of gripping teeth and the longitudinal axis of a plate essentially runs at right angles to the clamp slit for tissue formed by the gripping teeth. In this case the plates can be arranged in such a way that a plate is aligned with one of the gripping teeth in each case.

In another embodiment, the portion of the at least one force deflecting element made of bioresorbable material is configured in such a way that it replicates the zigzag shape of the gripping teeth on its side facing towards the gripping teeth or that it is also parallel to the clamp slit, while on its side facing the outer edge of the force deflecting element it replicates the shape of the outer edge of the force deflecting element.

For improved attachment of the portion of the at least one force deflecting element made of bioresorbable material to the portion made of non-bioresorbable material, the bioresorbable portion can be secured in position by at least one clamp made of a non-bioresorbable, tissue-compatible material.

In another embodiment, the portion of the at least one force deflecting element made of bioresorbable material is configured as two plates made of bioresorbable material attached on both outer sides to the portion made of non-bioresorbable material and permanently fixed to each other. Here the two plates of the portion of the at least one force deflecting element made of bioresorbable material are connected to each other and secured to the non-bioresorbable portion via at least one pin made of bioresorbable material by means of a medical adhesive, for example cyanoacrylate.

DESCRIPTION OF FIGURES

Other features and advantages of the present invention are illustrated by the following exemplary description of a particularly preferred embodiment of the invention based on the figures.

These are as follows:

FIG. 2 shows the view as a stamped part or laser-cut component made of a flat material. Further processing (embossment into a U profile) can create the functional shape, for example.

In terms of its basic design, with the exception of the integration of clip areas made of resorbable material, a preferred tissue clip of this type is generally known. For the purpose of better understanding, this clip is described in more detail with reference to FIG. 1a, which shows a possible clip design allowing the realization of the invention.

Figure 1A:
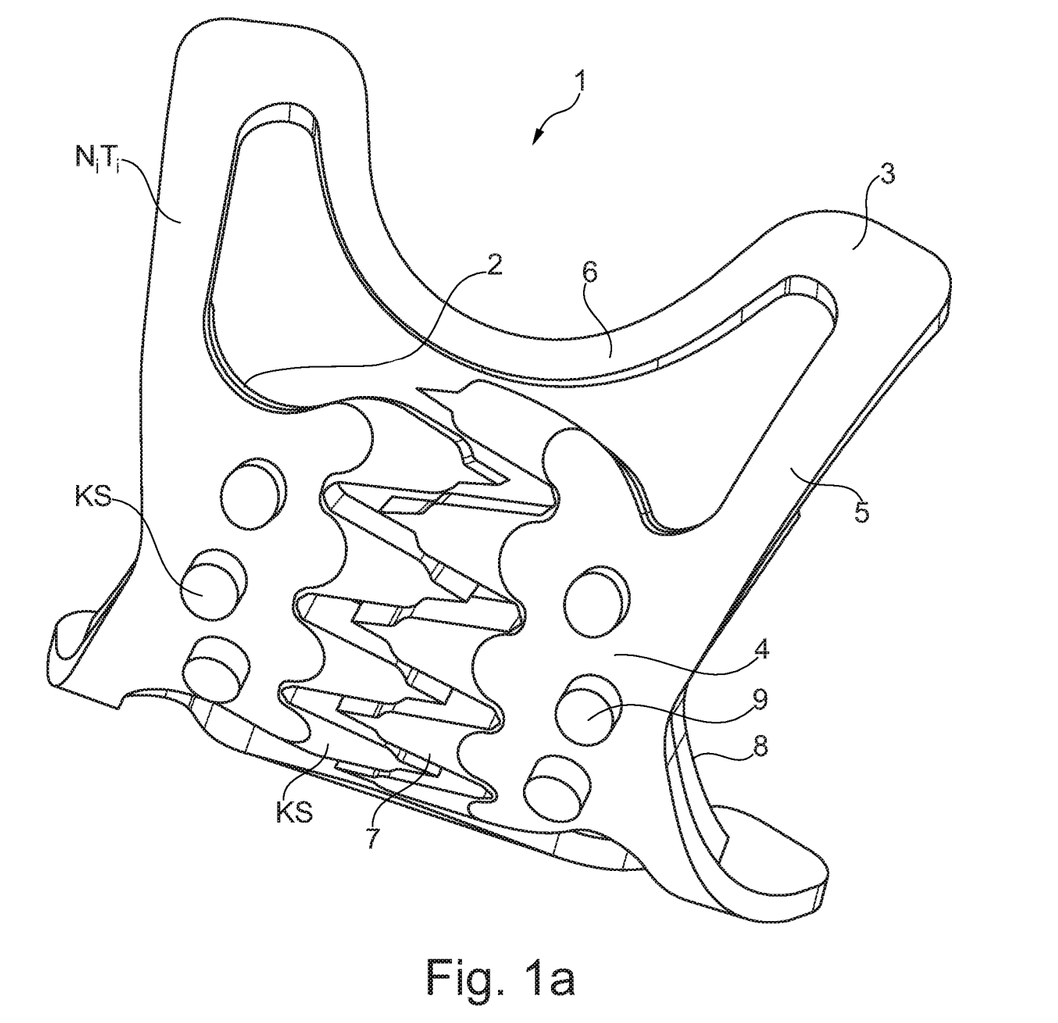
FIG. 1a shows a perspective view of a partly resorbable tissue clip with gripping teeth made of bioresorbable material and FIG. 1b shows a view of the lower side of the tissue clip from FIG. 1a, FIG. 2 shows a partly resorbable tissue clip in which a portion of each force deflecting element is configured as a flat cuboid made of bioresorbable material.

On this basis such a clip 1 according to this preferred variant consists of a mouth-type clamp device with two toothed jaws (force deflection elements) 4 which can be opened and closed via two side hinges 3, 5, 6 or via flexible mouldings. The hinges 3, 5, 6 or the flexible mouldings are preferably made of spring-biased bands which save the spring energy when the jaws 4 are opened and which cause to the jaws 4 to snap closed with a predefined clamping force when the jaws 4 are released, i.e. when the hinges 3, 5, 6 or the flexible mouldings are triggered.

Specifically, each clip 1 is punched or lasered in a single piece from a spring steel sheet by carving a ring out of the spring steel sheet with a partially differing ring width. Two diametrically opposite ring sections with a large ring width form the two jaws 4 (force deflection elements), while the two ring sections in between with a narrow ring width form the hinges 3, 5, 6 or the flexible (elastic) mouldings (bending springs). In particular, each hinge in this case consists of a C-shaped spring section 6 which runs via angular deflections 3 into a connecting section 5, which in turn finishes at the relevant jaw 4. The jaws 4 are configured in that the ring sections with large ring width are additionally curved in arc-like fashion on their flat side so as to form a circle when in an open state. This particular shaping of the lasered spring steel sheet creates the shape of a shark's mouth with two rows of teeth moving towards each other, formed by lasering of the ring sections with large ring width.

The operating principle of the above-described medical tissue clip 1 can be described as follows:

Generally speaking, an endoscopic implantation of a medical device is a procedure which only slightly affects the patient overall. In this case, the medical device has to be fixed to a hollow organ from the latter's inner side. For this purpose, a number (at least one) of the above-described tissue clamps, clips or anchors are introduced by means of an endoscope or another, preferably shaft-like feeder tool into the hollow organ and placed at predefined places on the inside of the organ. To this end, the clip or anchor in question is introduced to the organ tissue and the preload spring is triggered for a closing of the clip or span the anchor. The latter then holds or clamps a tissue fold between its jaws or its hooks or needles with a predefined clamping or spreading force, wherein the teeth, hooks, needles or prongs of each jaw sink into the tissue and preferably penetrate it.

At this point it should be pointed out that the tissue clip to which the invention is applied does not necessarily have to take the basic form described above but can also be configured in a different way, e.g. in the shape of a ring clasp with a number of radially inwardly protruding teeth spaced apart from each other peripherally which are formed on spring elements grouped to form a closed ring. However, the invention will be described below based on the mouth-shaped tissue clip.

FIG. 1a shows a perspective view of the partly resorbable tissue clip 1, comprising, according to the invention, a portion 2 made of a bioresorbable material and a portion 3 made of a non-bioresorbable material. In this embodiment, the non-bioresorbable portion 3 is preferably made as a single piece out of nitinol and the bioresorbable portion is made of a copolymer consisting of lactic and glycolic acid (PLGA). The non-bioresorbable portion 3 relates to the two force deflecting elements/tooth racks/jaws 4 and the two spring elements 6, wherein the two force deflecting elements 4 are arranged parallel to each other and are each connected to one end of one of the two spring elements 6 at their two longitudinal ends via the connection element 5. On the side facing the other force deflecting element 4, each of the two force deflecting elements 4 exhibits a number of gripping teeth 7. In this example, the gripping teeth 7 are made of the bioresorbable material.

The portion 2 of the tissue clip 1 made of bioresorbable material consists in this case of two elements which each comprise a row of gripping teeth 7 and a plate 8 made of bioresorbable material on which the respective gripping teeth are formed. Each of the elements of the bioresorbable portion 2 is made as a single piece, preferably made of PLGA. Each plate 8 is arranged parallel to one force deflecting element 4 in each case and exhibits a recess in which the force deflecting element 4 is embedded. The gripping teeth 7, made as a single piece with the plate 8, protrude from each of the force deflecting elements 4 in such a way that between the two force deflecting elements 4, arranged parallel to each other, a clamp slit for tissue is formed into which the gripping teeth 7 protrude. For permanent connection of a plate 8 to one force deflecting element 4 respectively, the plate 8 comprises at its end facing away from the gripping teeth 7 a recess/material abrasion 8a (see FIG. 1b) in which the force deflecting element 4 is inserted. In order to attach the force deflecting element 4 in the recess, the plate 8 has on the recess surface a number of pins/pegs 9 which engage into the relevant cut-outs in the respective force deflecting element 4 and secure the plate 8 to the force deflecting element 4 by means of interlocking.

Figure 1B:
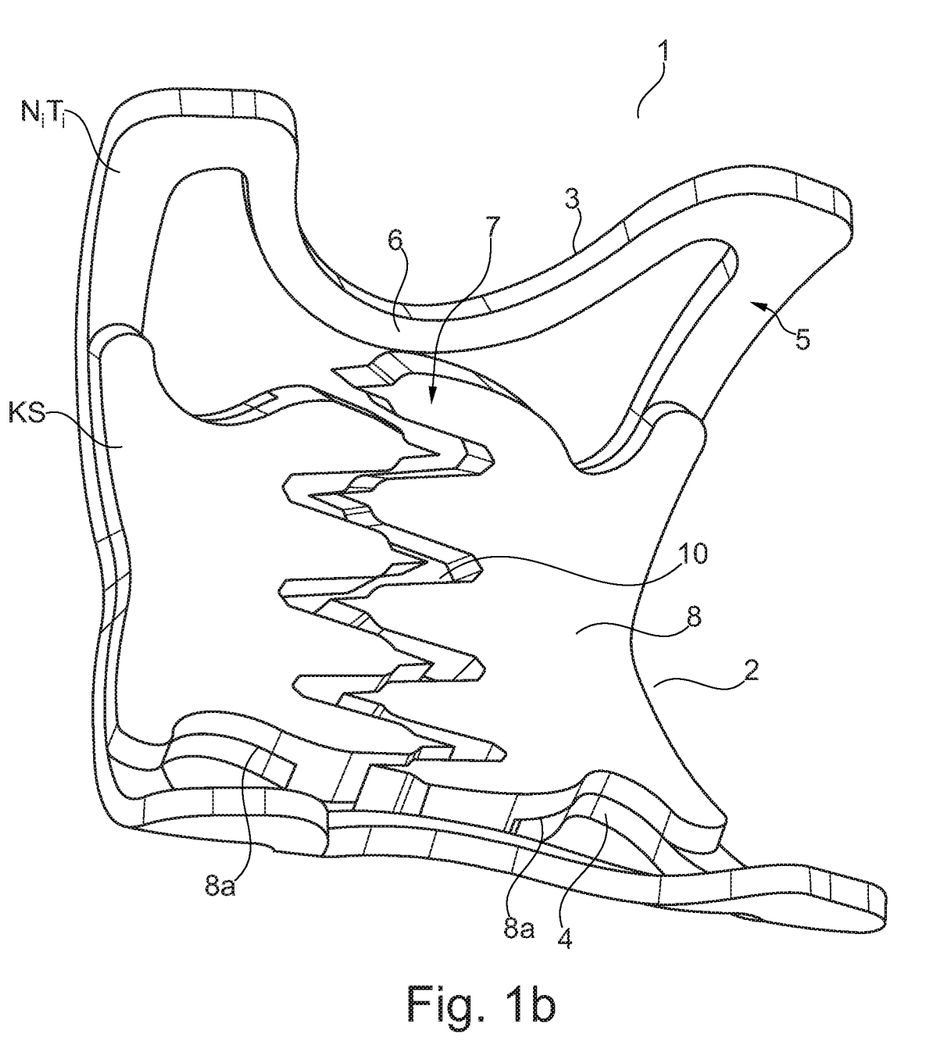

FIG. 1*b* shows the lower side/back of the tissue clip 1 shown in FIG. 1*a*. Here it can be clearly seen that the tissue clip 1 is composed of a single-section portion (clip frame) 3 made of non-resorbable material and a portion 2 made of bioresorbable material consisting of two elements, which are fixed to the non-resorbable clip portion 3. Each element of the bioresorbable portion is made as a single-section/unitary and exhibits the plate 8 and the number of gripping teeth 7 which protrude beyond the respective force deflecting element 4 and form the clamp slit 10 for tissue. In this depiction it can be seen that the plate 8 has in its section adjacent to the force deflecting element 4 a flat recess/material abrasion in which the force deflecting element 4 is embedded. The gripping teeth 7 and the plate 8 are made entirely of bioresorbable material. The recess in the plate 8 is configured such that the force deflecting element 4 embedded in the recess creates a continuous, smooth surface profile between the embedded force deflecting element 4 and each of the gripping teeth 7.

When such a tissue clip is used in practice, the teeth 7 penetrate into the patient tissue due to the spring force of the two spring elements 3, 5, 6 and become anchored there. In doing so, the gripping force extends beyond the plate 8 and the force deflection elements 4 as thrust forces, wherein the force deflecting elements 4 stabilize the plate 8 at the same time. When the absorbable material dissolves, at the end of the dissolving process only the non-absorbable clip portion is preserved whole, which can only exert a slight clamping force on the tissue. The clip can therefore easily detach itself from the tissue.

In order to improve the gripping effect of the gripping teeth 7, it can be advantageous to make the gripping teeth 7 from a non-bioresorbable material such as nitinol and instead, for the purpose of selective material weakening of at least one of the force deflecting elements, make at least one portion/area of this force deflecting element out of bioresorbable material.

Figure 2:
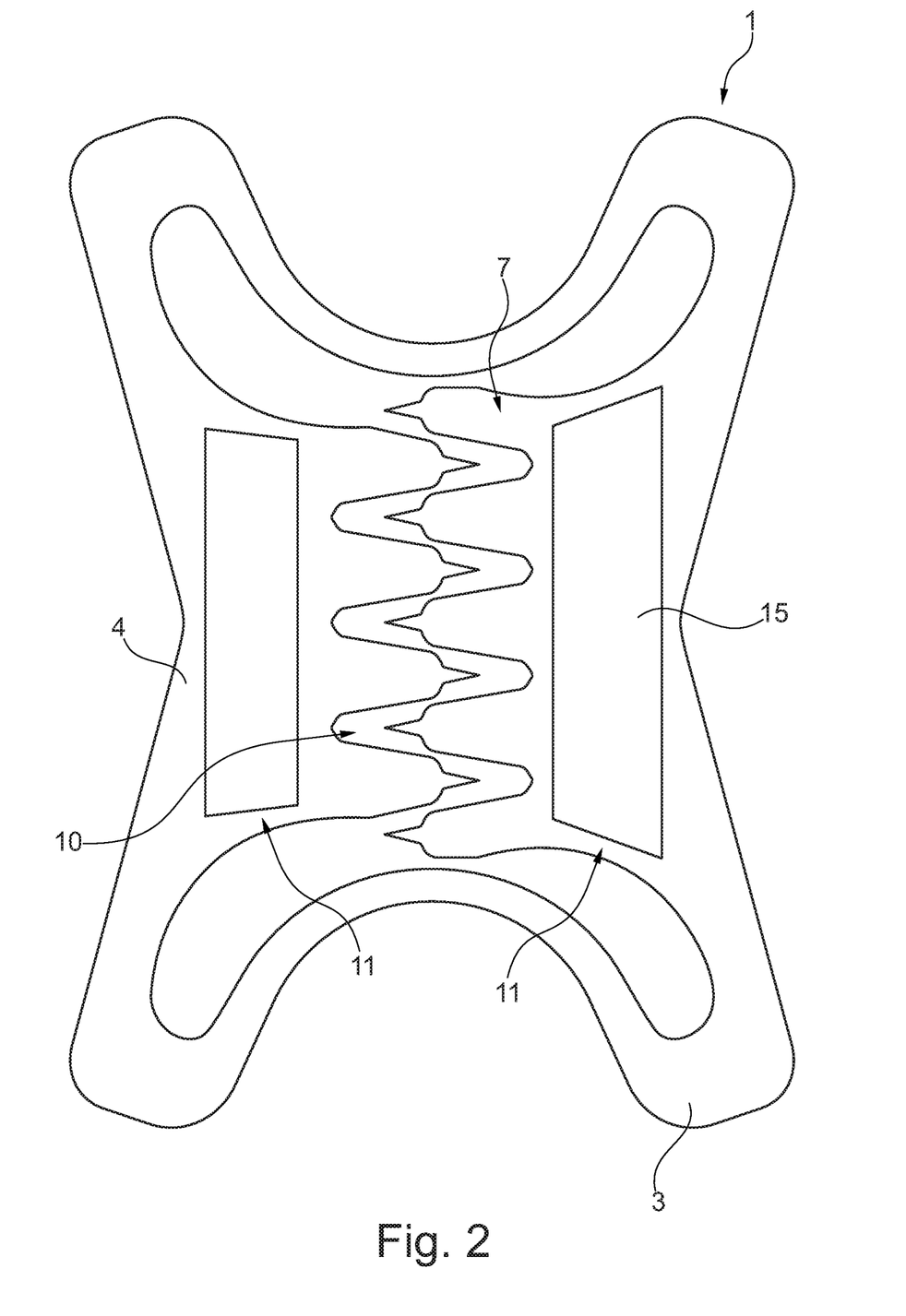

Such a tissue clip 1 with gripping teeth 7 made of non-resorbable material is shown in FIG. 2. The portion 2 made of bioresorbable material is configured here as two elements which each take the form of a flat cuboid (rectangular plate) 15 and which are each embedded/inserted in one of the force deflecting elements 4. Each of the force deflecting elements 4 exhibits a cut-out/window opening which corresponds to the shape of an element of the bioresorbable portion 2 in which an element of the bioresorbable portion 2 is embedded. The cut-out in the force deflecting element 4 can be produced, for example, by selective etching or die sinking/sinker electrical discharge machining (this would preferably create a profile that is potentially still closed around a whole area here, but the profile could be very thin as compared to the material thickness of the remainder of the clip, making it significantly more flexibly deformable; the resorbable portion would then fill up/compensate for the thinness of the material) or simply be cut out of the force deflection elements 4 (this then creates an open, window-shaped through-hole). The longitudinal axis of each element of the bioresorbable portion 2 embedded in the force deflecting element 4 preferably runs parallel to the clamp slit 10 for tissue formed by the gripping teeth 7. The two longitudinal edges of each element of the bioresorbable portion 2 essentially run parallel to each other. Here, each element of the bioresorbable portion 2 is formed in such a way that between each short edge of each element and the nearest short edge of the force deflecting element in which the element is embedded there is only a thin bar 11 made of non-bioresorbable material (formation of a frame structure in the respective force deflection element).

Once the bioresorbable portion 2 of the tissue clip 1 has been resorbed, the entire clamping/gripping force is applied to the thin bars between the window openings, which are elastically deformed/buckled as a result. As a result there is a decrease in the clamping force applied by the tissue clip 1 to the tissue and the tissue clip 1 detaches itself from the tissue. In order to reinforce this effect, the thin bars 11 can be made of nitinol or a material with a particularly high nitinol content. The thin bars 11 also prevent the clip from falling apart into several pieces of the non-bioresorbable portion 3 after resorption of the bioresorbable portion 2 of the tissue clip 1, so that the remaining portion 3 of the tissue clip 1 remains in a single piece and can be eliminated in the normal, secure way by the body.

Figure 3:
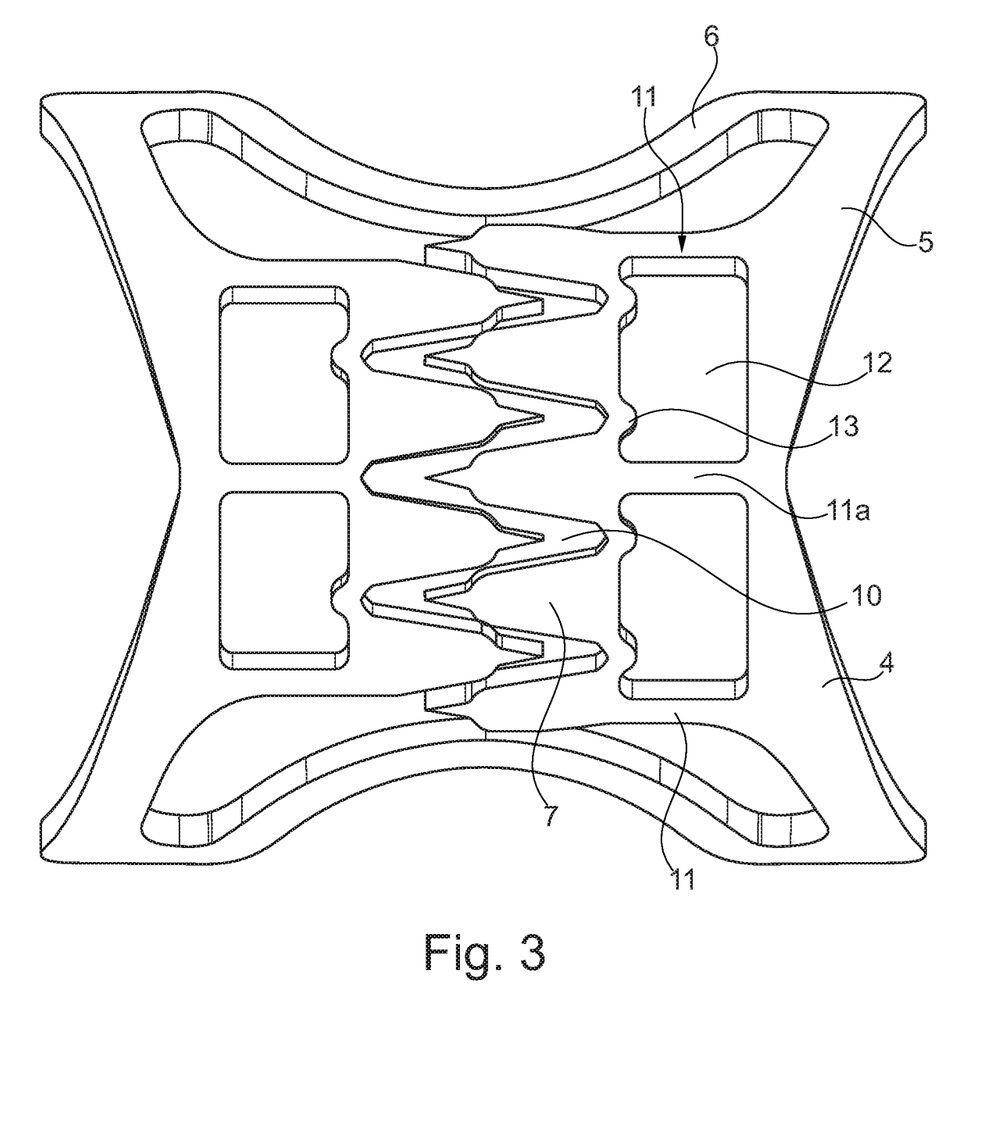
FIG. 3 shows a non-bioresorbable portion of a partly resorbable tissue clip in which a portion of each force deflecting element is configured as two flat cuboids arranged in series and made of bioresorbable material.

In order to improve the stability of the tissue clip 1 so that after resorption of the bioresorbable portion 2 it can exhibit improved clamping force, it is possible—as shown in FIG. 3—for the portion 3 of the tissue clip 1 made of non-bioresorbable material to comprise an additional thin bar 11*a* at the centre of each of the force deflecting elements 4 in addition to the thin bars 11 at the respective short edges of each force deflecting element 4. Here, each element of the bioresorbable portion 2 of the tissue clip 1 is configured as two flat cuboids (rectangular plates) 15 arranged in series and separated by the thin bar 11*a* arranged at the centre of the force deflecting element 4. In order to hold the plates 15 of the bioresorbable portion 2 arranged in series, each of the two force deflecting elements 4 comprises two cut-outs/window openings 12 arranged in series which correspond to the shape of the bioresorbable plates 15. The longitudinal axis of each cut-out 12 runs essentially parallel to the longitudinal axis of the clamp slit 10. For improved anchoring of each plate 15 of the bioresorbable portion 2 in one of the cut-outs 12 of a force deflecting element 4, the edge of each cut-out 12 facing the gripping teeth 4 exhibits one or more bulges 13 or position lugs which protrude into the cut-out 12 and are aligned with a channel of the zigzag shape defined by the gripping teeth 7. The plates 15 of the bioresorbable portion each exhibit one or more grooves in which one of the bulges 13 engages, thereby fixing the bioresorbable portion 2 to the non-bioresorbable portion 3.

Figure 4:
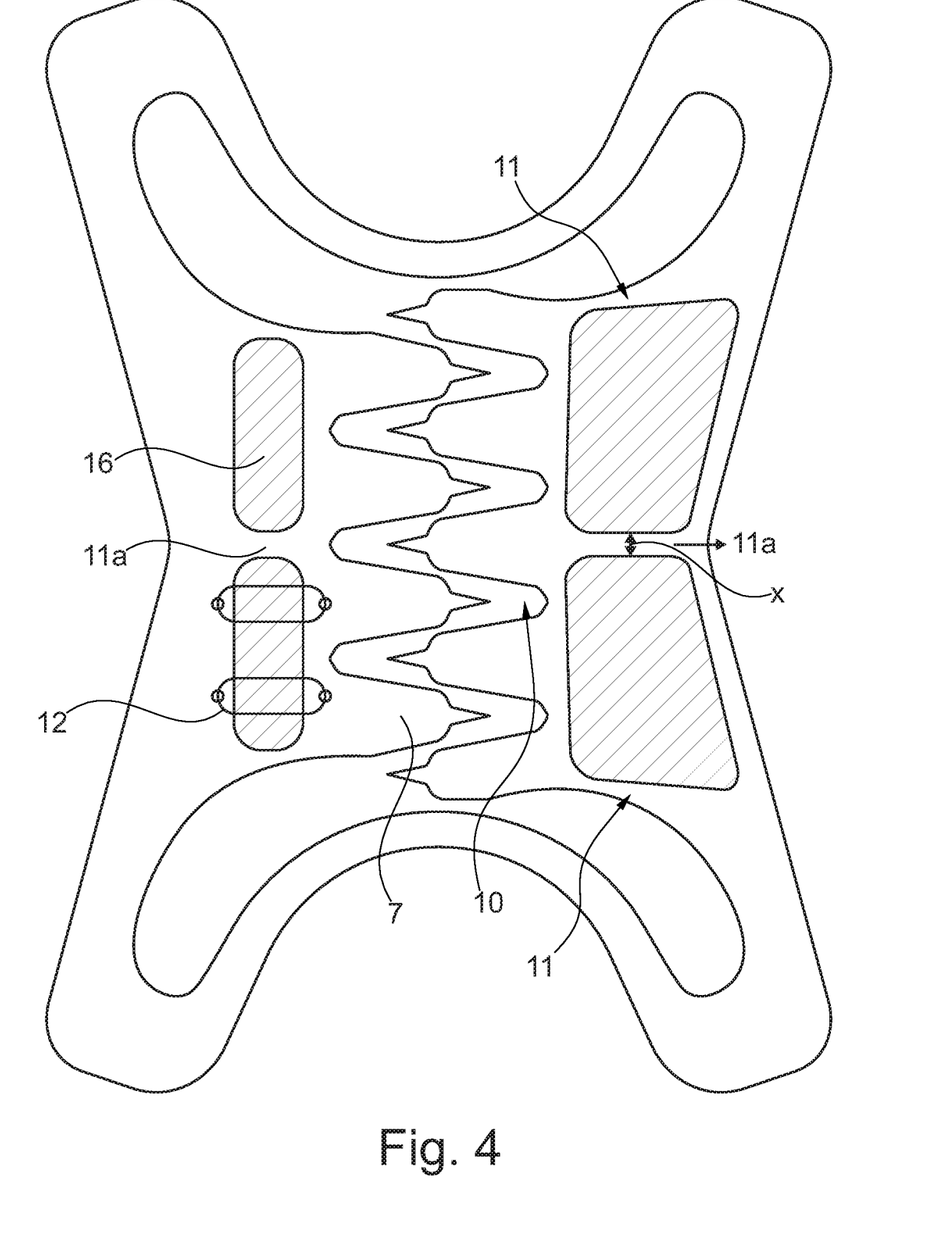
FIG. 4 shows a partly resorbable tissue clip in which a bioresorbable portion of a force deflecting element is configured as two dual-circle cuboids arranged in series and the bioresorbable portion of another force deflecting element is configured as two elements arranged in series which each run parallel to the clamp slit for tissue on their side facing the clamp slit for tissue and which run parallel to the outer edge of the force deflecting element on their side facing the outer edge of the force deflecting element.

As shown in FIG. 4, the exact shape of the elements of the bioresorbable portion 2 of the tissue clip 1 can be tailored to the needs of a specific application. It is also possible to insert differently shaped bioresorbable elements in different force deflecting elements 4. In a force deflecting element 4 in FIG. 4, for example, the cut-outs for holding the elements of the bioresorbable portion 2 are configured as two elongated holes arranged in series whose respective longitudinal axis run essentially parallel to the longitudinal axis of the clamp slit 10. Between the two elongated holes there is a thin bar 11*a*. Each of the bioresorbable elements is configured as a plate 16 corresponding to an elongated hole and embedded in an elongated hole. In addition, the non-bioresorbable portion 3 can exhibit clamps 12 by means of which the elements of the bioresorbable portion 2 are secured in the cut-outs of the non-bioresorbable portion 3.

Alternatively, the cut-outs in the non-bioresorbable portion 3 of the tissue clip 1 can be configured in such a way that the side of each cut-out facing the gripping teeth 7 runs essentially parallel to the longitudinal axis of the clamp slit 10. The short side facing the central thin bar 11*a* of each cut-out runs at right angles to the longitudinal axis of the clamp slit 10. The longitudinal side of each cut-out facing the outer edge of the force deflecting element 4 and the short side of each cut-out facing the outer thin bar 11 run essentially parallel to the nearest outer edge of the force deflecting element 4.

Figure 5:
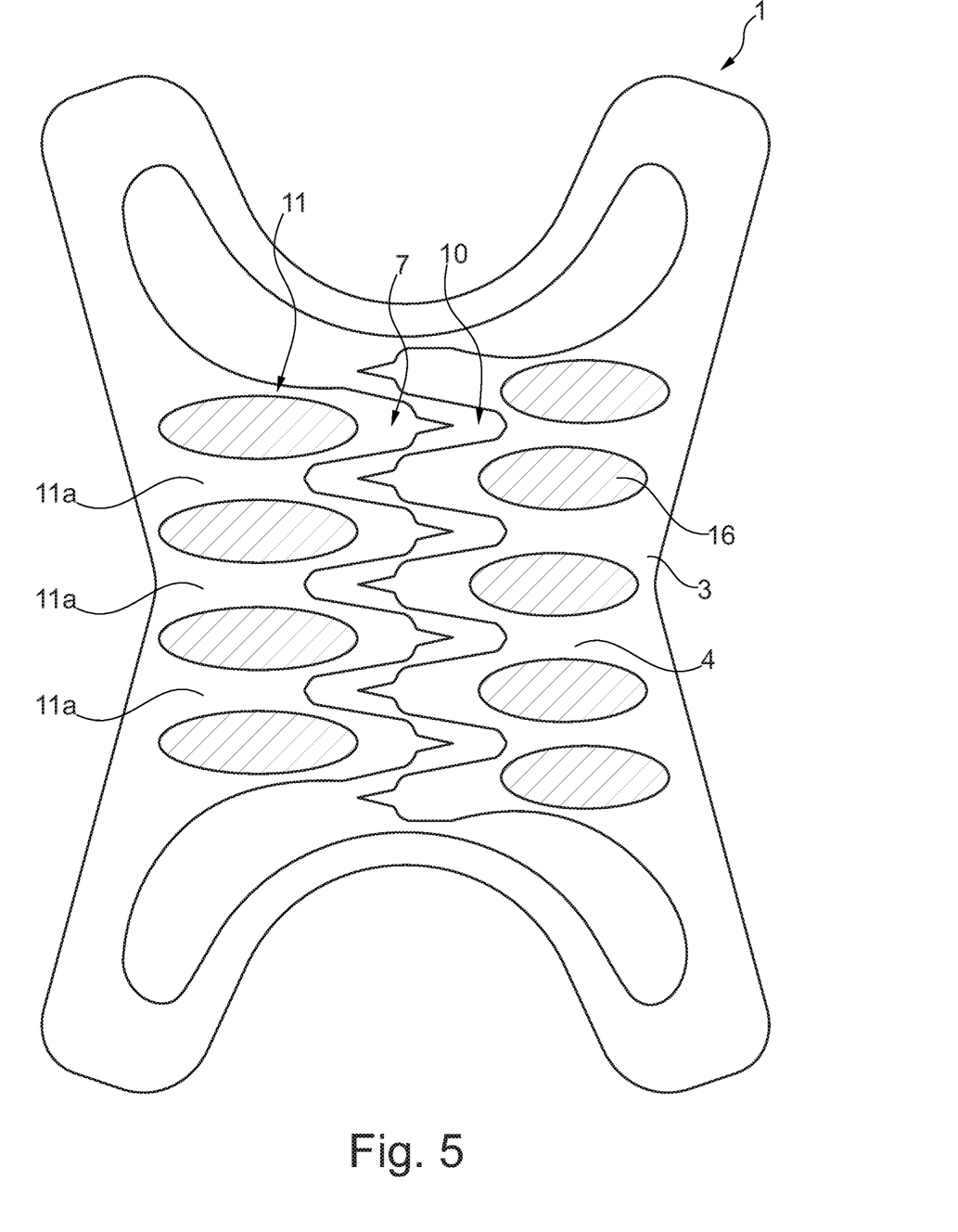
FIG. 5 shows a partly resorbable tissue clip in which the bioresorbable portion of each force deflecting element is configured as a number of dual-circle cuboids, each of which is aligned with a gripping tooth, wherein the number of dual-circle cuboids is equal to the number of gripping teeth and the longitudinal axis of each dual-circle cuboid runs essentially at right angles to the clamp slit for tissue formed by the gripping teeth.

FIG. 5 shows a tissue clip 1 in which the bioresorbable portion 2 consists of several flat plates 16 per force deflection element, each of which is embedded in a respective elongated hole in a force deflecting element 4. Here the longitudinal axis of each plate 16 runs essentially at right angles to the longitudinal axis of the clamp slit 10. Each plate 16 is arranged in such a way that it is aligned with a gripping tooth 7. Thin bars 11a separate a plate 16 from the next plate 16 in each case.

Figure 6:
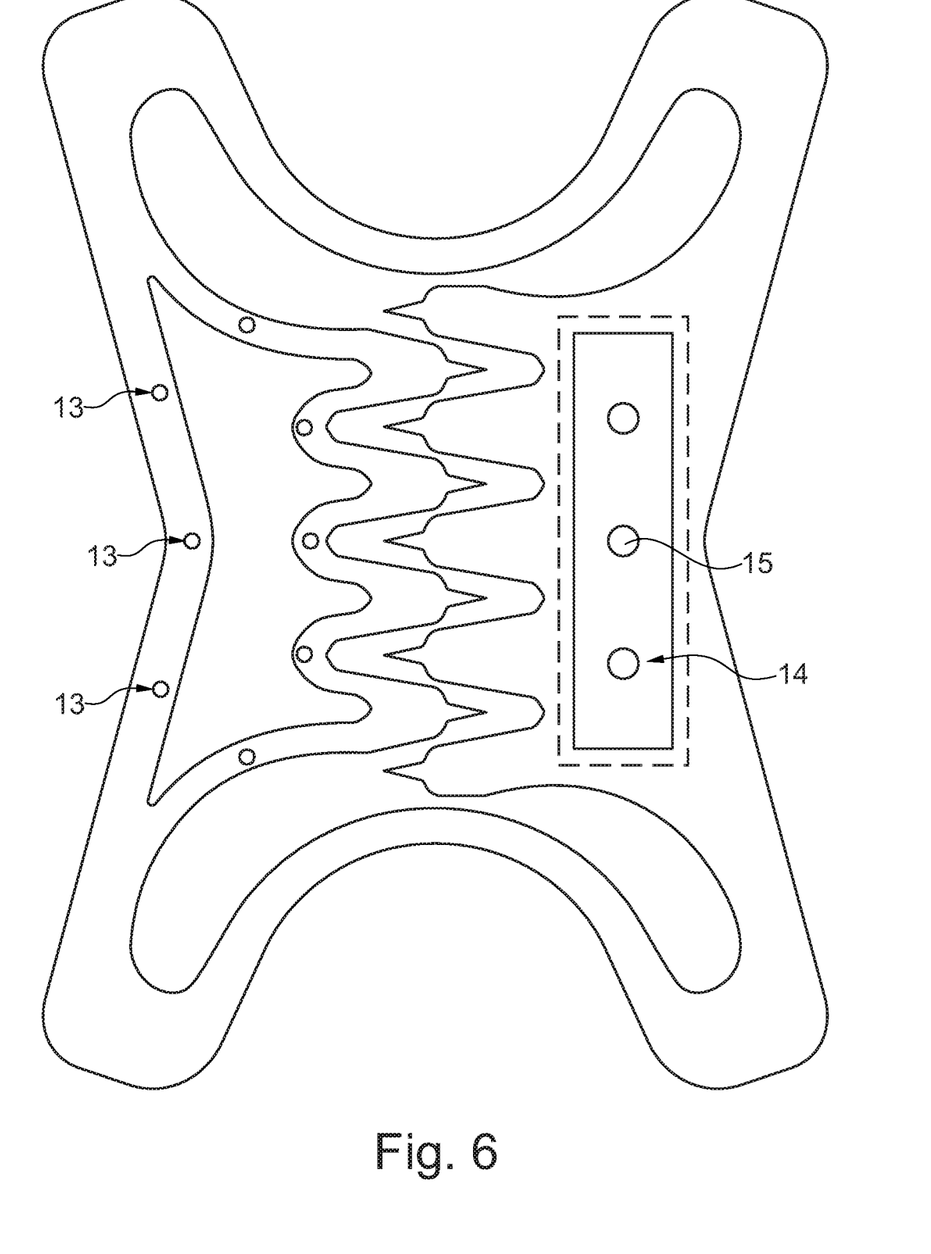
FIG. 6 shows a partly resorbable tissue clip in which a bioresorbable portion of a force deflecting element is configured in such a way that it replicates the zigzag shape of the gripping teeth on its side facing the gripping teeth, while on its side facing the outer edge of the force deflecting element it replicates the shape of the outer edge of the force deflecting element. The bioresorbable portion of another force deflecting element is configured as two plates made of bioresorbable material attached at the two outer sides to the portion made of non-resorbable material and permanently fixed to each other, wherein the two plates are connected to each other by three pins made of bioresorbable material by means of a medical adhesive, preferably cyanoacrylate, and secured on the non-bioresorbable portion.

FIG. 6 shows a tissue clip 1 in whose one force deflecting element 4 an element of a bioresorbable portion 2 is embedded, wherein this element is configured in such a way that it replicates the zigzag shape of the gripping teeth 7 on its side facing the gripping teeth 7, while on its side facing the outer edge of the force deflecting element 4 it replicates the shape of the outer edge of the force deflecting element. For improved fixing of the bioresorbable element in the force deflecting element 4, the cut-out in the force deflecting element exhibits pegs (pins) 13 at its inner edge which engage in corresponding holes in the element of the bioresorbable section 2 embedded in the cut-out. The element of the bioresorbable portion 2 embedded in the other force deflecting element 4 of the tissue clip 1 is configured as two plates 14 made of bioresorbable material attached by the two outer sides to the portion 3 made of non-resorbable material and permanently fixed to each other, wherein the two plates 14 extend beyond the periphery/circumference of the cut-out in the force deflecting element 4 (dotted line) and are connected to each other via three pins 15 made of bioresorbable material by means of a medical adhesive, preferably cyanoacrylate, and secured to the non-bioresorbable portion 3.

The invention claimed is:

1. A partly resorbable tissue clip, comprising:
a mouth-type clamp device having an upper and a lower jaw, the clamp device being adapted to be opened and closed via a hinge or flexible molding interconnecting the upper and lower jaws to snap into a closed position by accumulated spring energy thereby generating a predefined clamping force in between,
wherein the clamp device comprises a first portion formed from non-biologically resorbable material and the first portion formed from non-biologically resorbable material is a single piece forming a closed loop,
at a middle portion of each jaw, the first portion formed from non-biologically resorbable material provides a flat force deflecting element respectively being orientated parallel to each other such that both middle portions are facing each other edgewise,
a number of gripping teeth being provided at edges of the upper and lower jaws which face each other at least in the closed position of the jaws,
wherein the gripping teeth for each jaw are integrally formed at a first plate, respectively, both the gripping teeth and the first plates being made of biologically resorbable material.

2. The partly resorbable tissue clip of claim 1, wherein the non-biologically resorbable material is nitinol.

3. The partly resorbable tissue clip of claim 1, wherein the first portion produced from non-biologically resorbable material is produced in an integral manner, with an injection molding, punching or laser cutting method and forms a frame construction.

4. The partly resorbable tissue clip of claim 1, wherein the biologically resorbable material is a copolymer comprising poly lactic-co-glycolic acid (PLGA), hydroxyapatite (HPA), beta tricalcium phosphate, tricalcium phosphate (TCP) or polylactide.

5. The partly resorbable tissue clip of claim 1, wherein as a result of a selection of biologically resorbable material or a variation of a composition of biologically resorbable material, a time course of resorption and consequently the predefined clamping force of the tissue clip can be determined.

6. The partly resorbable tissue clip of claim 1, wherein the biologically resorbable material contains medical active ingredients which are locally released over time by resorption of the material or diffusion from said material.

7. The partly resorbable tissue clip of claim 1, wherein at least one of the upper or lower jaws comprises a second portion produced from biologically resorbable material and constructed substantially as a second plate, whose longitudinal axis extends parallel with a clamping slot formed by the gripping teeth.

8. The partly resorbable tissue clip of claim 7, wherein the second portion produced from biologically resorbable material is constructed as two flat second plates which are arranged beside each other and whose longitudinal axes extend parallel with the clamping slot formed by the gripping teeth.

9. The partly resorbable tissue clip of claim 7, wherein the second portion produced from biologically resorbable material is held in position by at least one clip which is produced from a non-biologically resorbable material.

10. The partly resorbable tissue clip of claim 7, wherein the second portion produced from biologically resorbable material at a side thereof facing the gripping teeth follows a curve shape of the gripping teeth, and at a side thereof facing an outer edge of the at least one of the upper or lower jaws, the second portion follows a shape of a nearest outer edge of the at least one of the upper or lower jaws.

11. The partly resorbable tissue clip according to claim 1, wherein the first plates are integrally formed and are fixed to the force deflecting elements in a planar manner.

12. The partly resorbable tissue clip of claim 1, wherein the plates and the force deflecting elements comprise projections and/or rejections being adapted to interconnect each other to provide a form-interlock when the plates are mounted at the force deflecting elements, respectively.

13. The partly resorbable tissue clip of claim 1, wherein the plates and the force deflecting elements are connected to each other by welding.

14. The partly resorbable tissue clip of claim 1, wherein each flat force deflecting element is formed as a curved plate.

* * * * *